(12) United States Patent
Hong et al.

(10) Patent No.: US 11,493,490 B2
(45) Date of Patent: Nov. 8, 2022

(54) ELECTRONIC NOSE APPARATUS BASED ON SPECTRUM ANALYSIS AND METHOD OF IMPLEMENTING THE SAME

(71) Applicant: ELECTRONICS AND TELECOMMUNICATIONS RESEARCH INSTITUTE, Daejeon (KR)

(72) Inventors: Hyo Bong Hong, Daejeon (KR); Jae Chan Jeong, Daejeon (KR); Seung Min Choi, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 309 days.

(21) Appl. No.: 16/842,476

(22) Filed: Apr. 7, 2020

(65) Prior Publication Data
US 2021/0048418 A1  Feb. 18, 2021

(30) Foreign Application Priority Data
Aug. 14, 2019 (KR) .................. 10-2019-0099934
Jan. 31, 2020 (KR) .................. 10-2020-0011686

(51) Int. Cl.
*G01N 33/00*  (2006.01)
*G01N 1/40*  (2006.01)
*G01H 3/00*  (2006.01)
*G01H 3/04*  (2006.01)
*G01H 13/00*  (2006.01)

(52) U.S. Cl.
CPC ............ *G01N 33/0001* (2013.01); *G01H 3/00* (2013.01); *G01H 3/04* (2013.01); *G01H 13/00* (2013.01); *G01N 1/4055* (2013.01); *G01N 33/0031* (2013.01)

(58) Field of Classification Search
CPC ............ G01N 33/0001; G01N 1/4055; G01N 33/0031; G01H 3/00; G01H 3/04; G01H 13/00
See application file for complete search history.

(56) References Cited

U.S. PATENT DOCUMENTS

| | | | | |
|---|---|---|---|---|
| 4,895,017 A * | 1/1990 | Pyke | ..................... | G01N 29/022 73/24.06 |
| 2008/0105029 A1* | 5/2008 | Kober | .................. | G01N 29/036 73/19.03 |

(Continued)

FOREIGN PATENT DOCUMENTS

| | | | |
|---|---|---|---|
| JP | 2018072310 A | | 5/2018 |
| KR | 101791615 B1 | | 10/2017 |

(Continued)

*Primary Examiner* — Benjamin R Schmitt

(57) ABSTRACT

In an electronic nose apparatus and method based on spectrum analysis, 1) a gaseous sample is dissolved into a solvent in an impinger, and the sample dissolved into the solvent is introduced into an RF resonator, and 2) RF having various absorption spectra according to materials are generated in the RF resonator, and the type of gas is determined through spectrum analysis so that an electronic nose is implemented. In this way, it is possible to overcome the resolution of gas chromatography (GC) and a sensor array and a limited number of multi-channel sensors (the number of channels).

16 Claims, 8 Drawing Sheets

(56) References Cited

U.S. PATENT DOCUMENTS

2014/0062666 A1* 3/2014 Patterson ........... G06K 7/10366
340/10.1
2017/0343521 A1 11/2017 Chang et al.
2018/0180491 A1* 6/2018 van der Weide .. G06K 7/10366

FOREIGN PATENT DOCUMENTS

KR         101852074 B1    4/2018
KR         101941158 B1    4/2019
WO    WO-9306504 A1 *   4/1993  ............ C30B 29/18

* cited by examiner

ELECTRONIC NOSE APPARATUS BASED ON SPECTRUM ANALYSIS AND METHOD OF IMPLEMENTING THE SAME

CROSS-REFERENCE TO RELATED APPLICATION

This application claims priority to and the benefit of Korean Patent Applications No. 10-2019-0099934 filed on Aug. 14, 2019, and No. 10-2020-0011686 filed on Jan. 31, 2020, the disclosures of which are incorporated herein by reference in its entirety.

BACKGROUND

1. Field of the Invention

The present invention relates to a technology for implementing an electronic nose on the basis of electromagnetics, electronic and electrical engineering, medical engineering, and material engineering, and more particularly, to an electronic nose apparatus based on spectrum analysis and a method of implementing the same.

2. Discussion of Related Art

The human nose is a very sensitive organ among sense organs and reacts to chemical substances in a gaseous state. However, the human nose basically has a sensing time which is relatively very short, and particularly, when a person tests a toxic material in person, his or her health is threatened. Also, the human nose does not have the ability to analyze the composition of chemical substances and thus entirely depends on the feeling and memory of the person who smells. Consequently, the human nose cannot provide an objective index. However, scent is a very important element in the food and cosmetic industries, and it is necessary to establish consistent and scientific data in order to use scent in industrial fields.

For this reason, efforts have been made in many sectors to develop an apparatus that is a so-called "electronic nose," and some electronic noses are available on the market. Current electronic noses can be generally classified into two types. One type is equipment which employs gas chromatography (GC) or GC-mass spectrometry without change and which has been remodeled for gaseous sample introduction instead of liquid sample introduction. In the other type, a sensor (or a sensor array) reacting to a gaseous material and a gas pump are combined to so that the reaction of the sensor is generated as data to obtain profiling data.

The GC or GC-mass equipment is very expensive and must use data measured by a mass or general detector over time by passing high-pressure gas through a GC-column (within several minutes to several hours). Also, it is not possible to interpret measured data without a specialist who has been educated to a very high level.

In the electronic nose which employs a sensor array, only tens of kinds of sensors can be installed, whereas an aromatic material is composed of several to thousands of kinds of chemicals. Consequently, in practice, it is significantly difficult to apply the electronic nose employing a sensor array to food, cosmetics, etc. having a complex scent.

SUMMARY OF THE INVENTION

The present invention is directed to solving two problems of existing electronic noses, that is, 1) the fundamental problems of gas chromatography (GC) or GC-mass analysis (the problem of an analysis time of tens of minutes to several hours and the problem of having to handle high-priced and high-pressure gas) and 2) the problem of being unable to be used for various uses due to the limited number of sensors.

To solve the problems, an electronic nose technology of the following process is provided.

1) A gaseous sample is dissolved into a solvent in an impinger, and the sample dissolved into the solvent is introduced into a radio frequency (RF) resonator so that physical and chemical features of the sample solution are changed.

2) RFs or electromagnetic waves having various absorption spectra according to materials are generated in the RF resonator, and the type of gas is determined through spectrum analysis so that an electronic nose is implemented.

According to an aspect of the present invention, there is provided an electronic nose based on spectrum analysis, the electronic nose including: an RF resonator configured to receive a test sample whose smell is to be measured and output an RF having a spectrum generated according to the received sample by resonating an applied RF with the received sample; and a signal generator/analyzer configured to apply the RF into the RF resonator and receive and analyze the RF output from the RF resonator through the resonance.

The electronic nose may additionally include an impinger configured to emit a sample, which is liquefied by concentrating a gaseous test sample whose smell will be measured into a solvent, to the RF resonator.

The electronic nose may additionally include an air pump configured to supply air to the impinger in order to emit the sample liquefied in the impinger.

In this way, it is possible to overcome the resolution of GC and sensor array, and a limited number of multi-channel sensors (the number of channels). Also, time taken to analyze spectrum is reduced to 1 to 2 seconds, that is, real-time analysis is enabled in practice. Consequently, applicability for industrial and research uses is increased, and it is possible to readily analyze various kinds of smells without replacing parts or sensors of existing equipment.

The above-described configurations and operations of the present invention will become more apparent from embodiments described in detail below with reference to the drawings.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
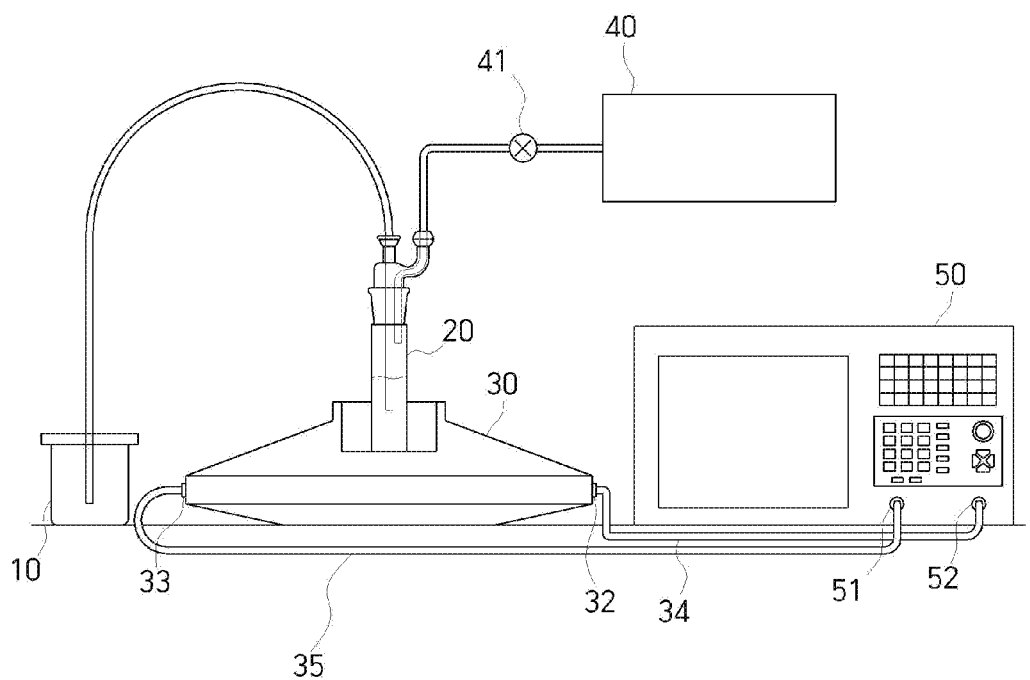
FIG. 1 shows a configuration of an overall system.

Advantages and features of the present invention and methods for achieving them will be made clear from embodiments described in detail below with reference to the accompanying drawings. However, the present invention may be embodied in many different forms and should not be construed as being limited to the embodiments set forth herein. Rather, these embodiments are provided so that this disclosure will be thorough and complete and will fully convey the scope of the present invention to those of ordinary skill in the technical field to which the present invention pertains. The present invention is defined by the claims.

Meanwhile, terms used herein are for the purpose of describing the embodiments and are not intended to limit the present invention. As used herein, the singular forms include the plural forms as well unless the context clearly indicates otherwise. The term "comprise" or "comprising" used herein does not preclude the presence or addition of one or more other elements, steps, operations, and/or devices other than stated elements, steps, operations, and/or devices.

Hereinafter, exemplary embodiments of the present invention will be described in detail with reference to the accompanying drawings. In adding reference numerals to elements of each drawing, the same elements may have the same reference numeral as possible even if the elements are shown in different drawings. Further, in describing the present invention, the detailed description of a related known configuration or function will be omitted when it obscures the gist of the present invention.

FIG. 1 shows an overall system configuration of an electronic nose according to the present invention.

The electronic nose includes a sample jar 10 containing a test gas which is to be smelled by the electronic nose, an impinger 20 which concentrates a gaseous sample contained in the sample jar 10 into a liquid solvent, an air pump 40 which supplies air to the impinger 20 in order to emit a liquefied sample in the impinger 20 (more exactly, in order to introduce the liquefied sample into a radio frequency (RF) resonator 30 which will be described below), an air regulator 41, such as a valve or a nozzle, for adjusting the amount of sample emitted from the impinger 20 by adjusting the amount of air emitted from the air pump 40, the RF resonator 30 which receives the sample introduced from the impinger 20 to measure the gaseous sample concentrated into the solvent in the impinger 20 and outputs an RF having a spectrum generated according to the received sample by resonating an applied RF (an electromagnetic wave or microwave) with the received sample, and a signal generator/analyzer 50 which applies the RF into the RF resonator 30 and receives and analyzes the RF which is output from the RF resonator 30 through the resonance.

Figure 2:
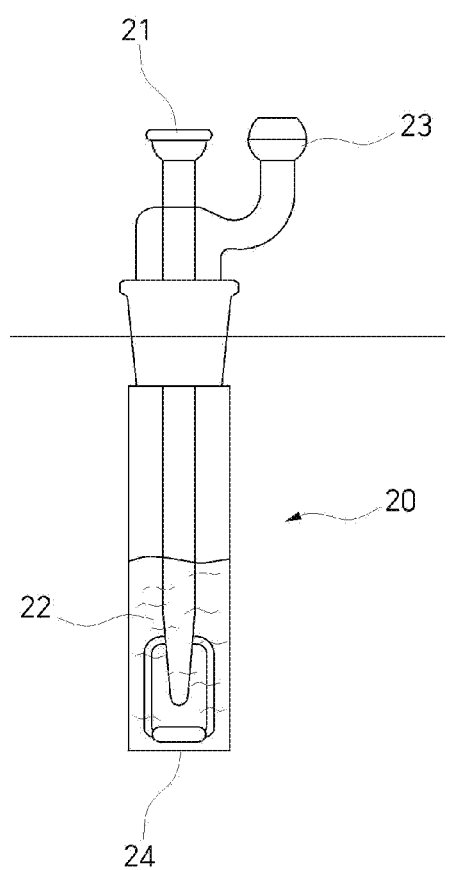
FIG. 2 shows a configuration of an impinger.

FIG. 2 shows a configuration of the impinger 20 according to an embodiment.

The impinger 20 is a type of glassware having a structure which dissolves a gaseous sample material flowing (from the sample jar 10) to a sample inlet 21 into a liquid solvent 22. As the solvent 22 for dissolving the gaseous sample, water is used when the sample is soluble in water, and acetone is used when the sample is soluble in fat.

The sample which is dissolved into the solvent 22 in the impinger 20 and liquefied is introduced from the sample outlet 24 into the RF resonator 30 through a sample injection hole 31 (see FIGS. 3A and 3B) of the RF resonator 30. To introduce the sample, air is injected to an air inlet 23 of the impinger 20 by the air pump 40 shown in FIG. 1. In this case, the amount of air input is controlled by the air regulator 41 (a nozzle or valve) of the air pump 40.

Figure 3A:
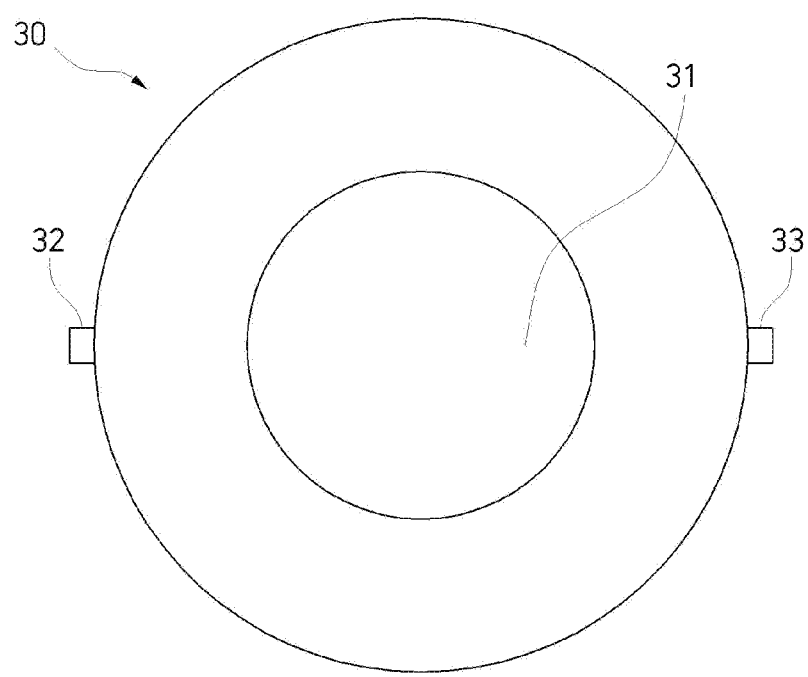
FIGS. 3A and 3B show a configuration of a radio frequency (RF) resonator.
Figure 3B:
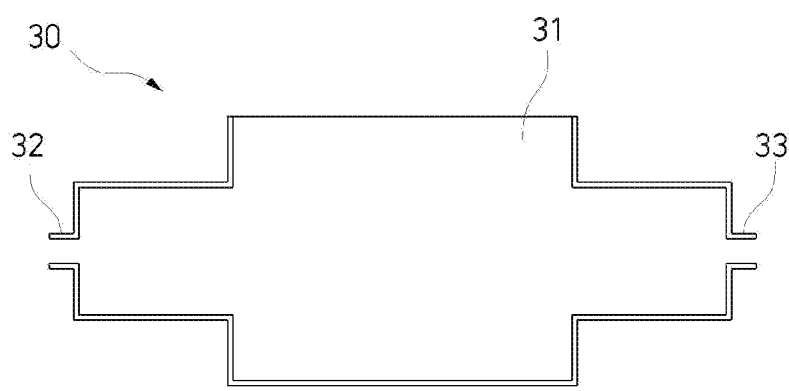

FIGS. 3A and 3B are diagrams showing a configuration of the RF resonator 30 according to an embodiment. FIG. 3A is a plan view, and FIG. 3B is a front view.

In this embodiment, the RF resonator 30 is made of a metal, such as aluminum or brass, in a nearly cylindrical shape so that an RF, such as an electromagnetic wave, etc., applied into the RF resonator 30 does not escape from the RF resonator 30 and forms a specific mode.

Specifically, the RF resonator 30 includes the sample injection hole 31 from which a sample is introduced from the impinger 20 shown in FIG. 1 into the RF resonator 30, an RF reception (RX) terminal 32 to which an RF, such as an electromagnetic wave, is input from the signal generator/analyzer 50 shown in FIG. 1, and an RF transmission (TX) terminal 33 which outputs an RF from the RF resonator 30 to the signal generator/analyzer 50.

An RX antenna and a TX antenna are respectively connected to the RF RX terminal 32 and the RF TX terminal 33 and thus connected to the signal generator/analyzer 50. The RX and TX antennas are connected to the signal generator/analyzer 50 in a wired or wireless manner.

In the case of a wired manner, the RX and TX antennas may be cables 34 and 35 (see FIG. 1) connected to an RF-Out receptacle 51 and an RF-In receptacle 52 of the signal generator/analyzer 50. In the case of a wireless manner, the RX and TX antennas may be, for example, circular antennas (e.g., a loop antenna) formed by coating a copper core with enamel to have a diameter of 3 cm to 5 cm.

When circular antennas are manufactured with metal wires as the wireless antennas, the diameter may be the maximum width (maximum diameter) of the wing of the RF resonator 30 or less (in this case, the antennas do not touch a metal surface of the RF resonator 30). As another embodiment, in the case of the wireless antennas, well-known broadband antennas may be used.

Meanwhile, the signal generator/analyzer 50 supplies an RF of a specific band (8 GHz to 35 GHz in the present invention) required for a resonance operation of the RF resonator 30. In this case, the RF may be supplied to the RF resonator 30 in certain frequency units (e.g., in units of 1 Hz). Also, the signal generator/analyzer 50 analyzes absorptivity from the spectrum of the RF signal. In this analysis, an S21 Mode may be used.

As the signal generator/analyzer 50, a vector network analyzer (VNA) may be used. In other specific situations, however, it is possible to acquire similar results with a scalar network analyzer (SNA) that phase information is not involved.

<Verification Experiment>

To verify the electronic nose apparatus based on spectrum analysis and the method of implementing the same according to the present invention, two kinds of scent that can be purchased on the market, that is, a wintergreen scent and a camphor scent were prepared.

The system was configured as shown in FIG. 1, and a sample which had been dissolved into a solvent in the impinger 20 without any preprocessing (acetone had been used as the solvent for dissolving the two gaseous samples) was introduced into the RF resonator 30 for 30 seconds by using the air pump 40. The sample introduction was stopped, and the wavelength region of 5 GHz to 6 GHz was swept in units of 10 MHz by using a VNA as the signal generator/analyzer 50.

Figure 4:
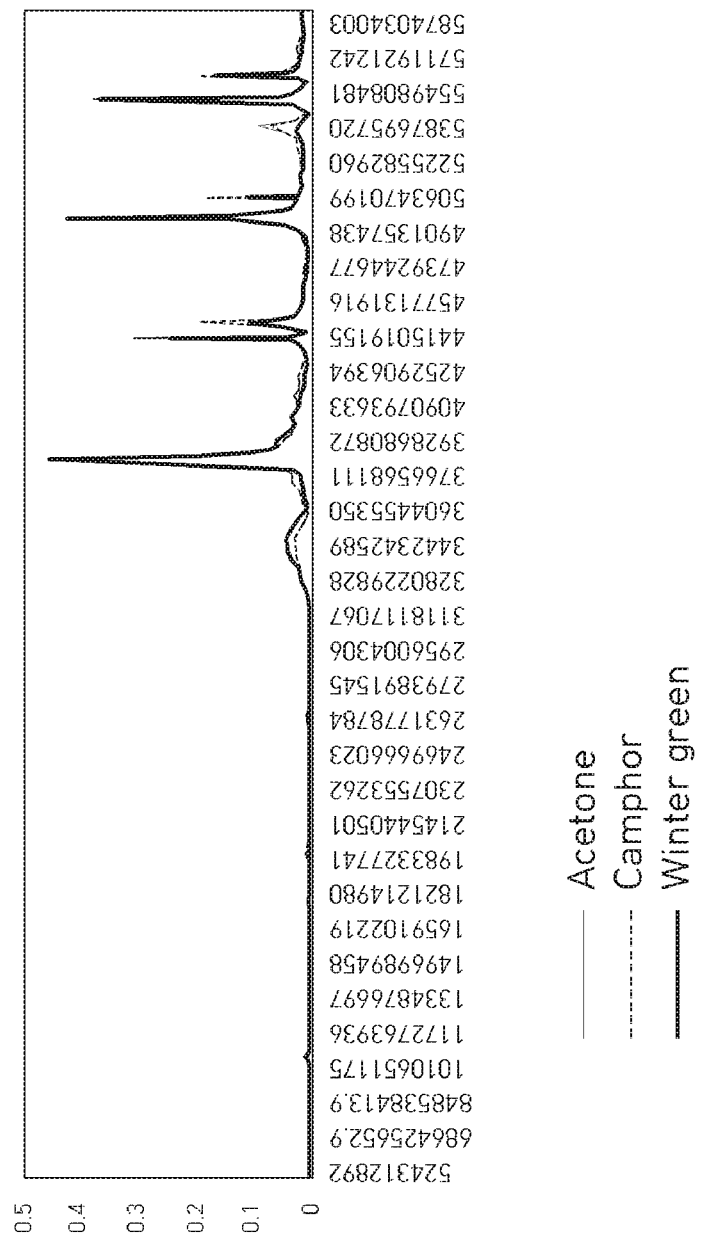
FIGS. 4 to 7 show materials for an experiment of the present invention and result graphs.

As a consequence of the above, spectrum distribution results of the camphor scent and the wintergreen scent were obtained as shown in FIG. 4. Here, the x-axis indicates RF frequency, and the y-axis indicates signal intensity. In the overall spectrum of FIG. 4, it is only possible to see difference between the samples. However, when the overall spectrum is divided into various frequency regions, it is possible to obtain detailed information as follows.

Figure 5:
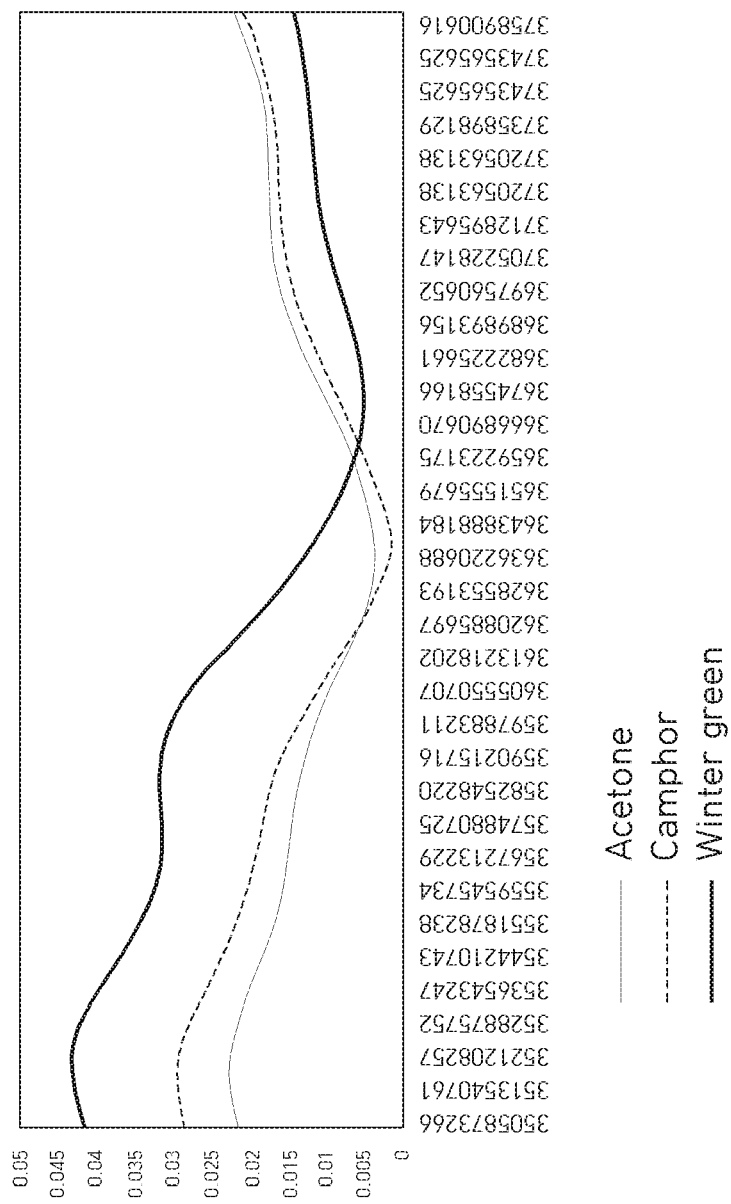

FIG. 5 shows comparative results among acetone (solvent), the camphor scent, and the wintergreen scent in the 35 to 37 GHz region.

Figure 6:
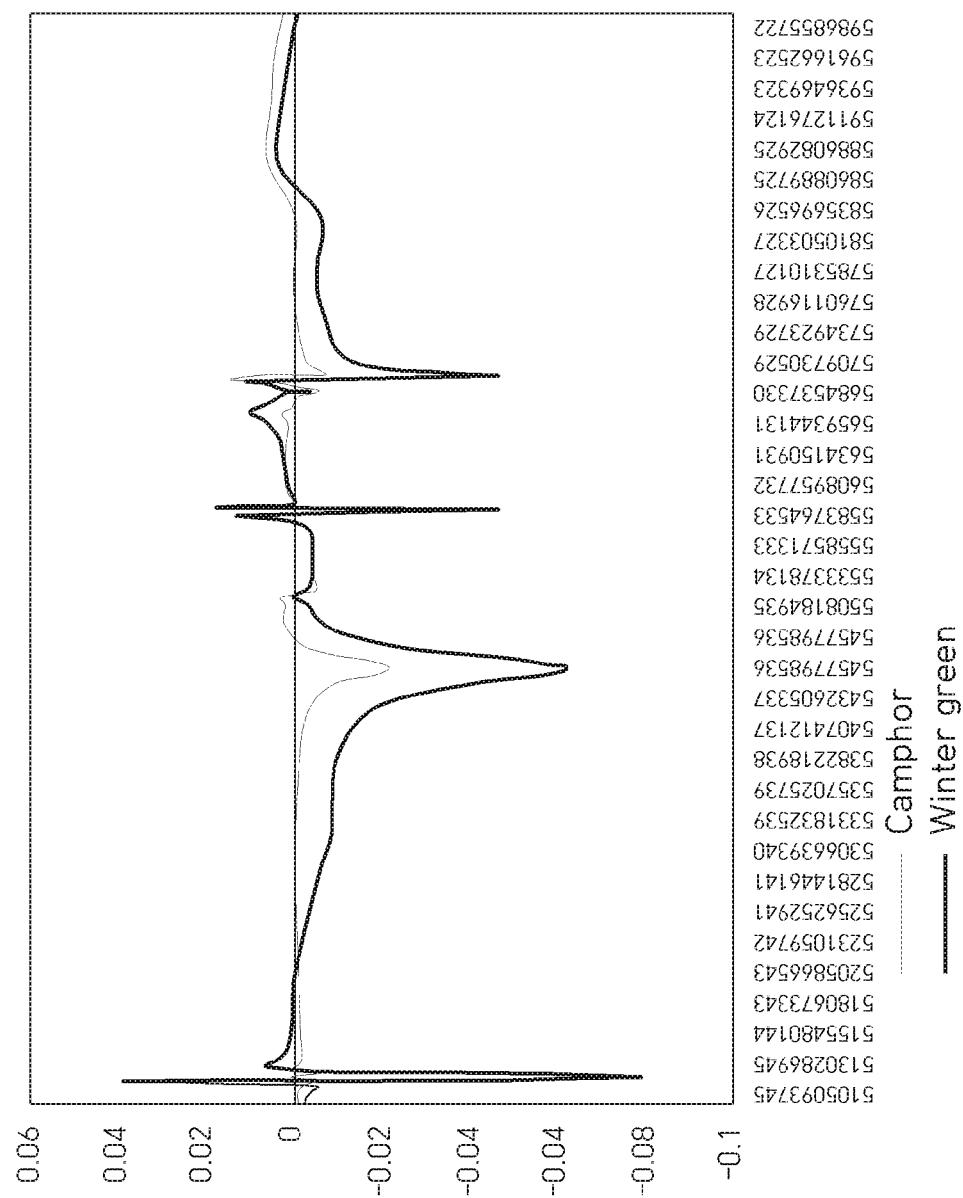

FIG. 6 is a comparison graph showing values obtained by subtracting the intensity value of acetone (solvent) from intensity values of the camphor scent and the wintergreen scent in the 51 to 60 GHz region.

Figure 7:
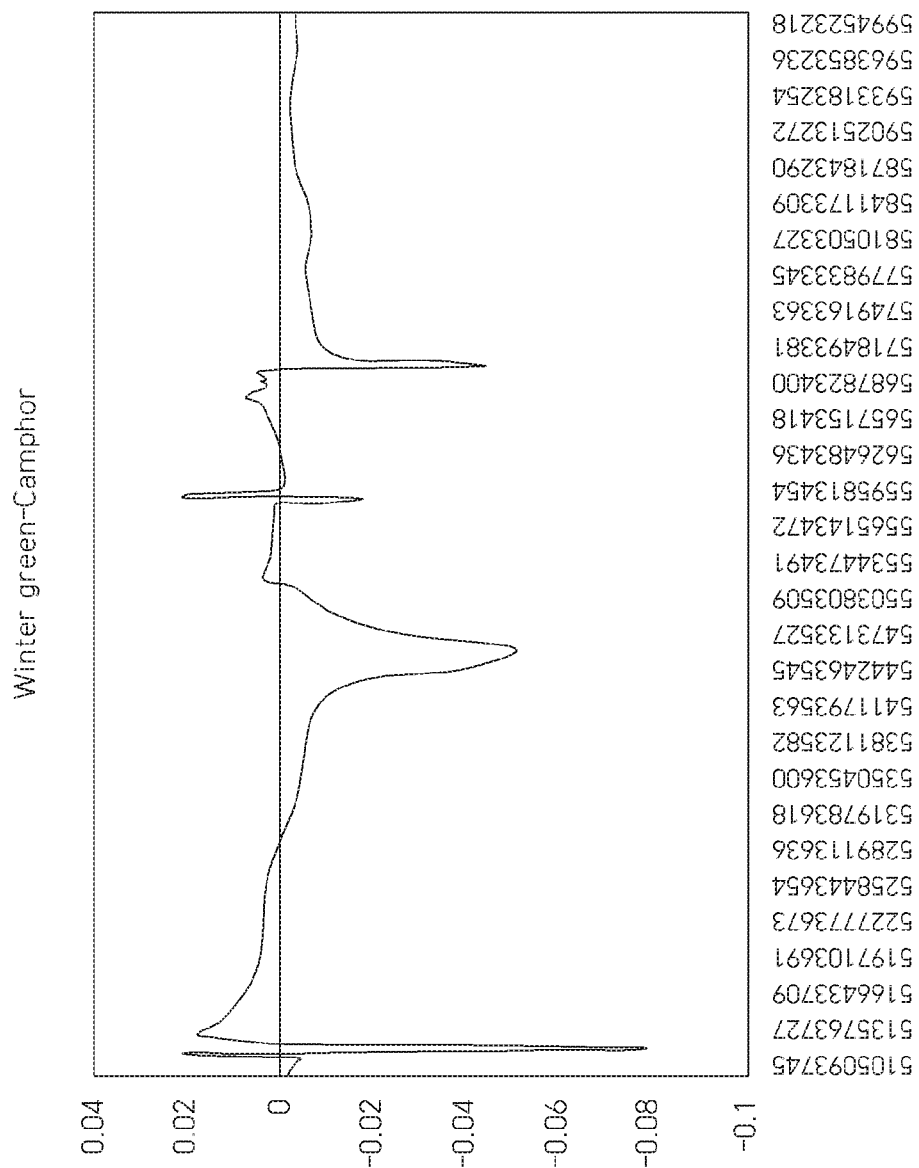

FIG. 7 is a graph showing results obtained by subtracting the intensity of the camphor scent from the intensity of the wintergreen scent in the graph of FIG. 6. The graph of FIG. 7 shows intensity difference according to frequency.

In the present invention, expensive equipment using gas chromatography mass spectrometry (GC-MS), which is considered as basic technology of existing electronic noses, is not used, and a GC column, carrier gas, etc. which are necessary for operation are not used. Consequently, the equipment price and operating cost become very low. Unlike an array sensor system which is considered as another basic form of electronic nose, the present invention does not employ many sensor systems but employs various frequencies generated from an RF resonator. Consequently, the present invention is advantageous in terms of equipment cost and operation. Also, optimal analysis which is appropriate for the features of a gaseous material is allowed by replacing a solution in an impinger.

Although the present invention has been described in detail above with reference to the exemplary embodiments, those of ordinary skill in the technical field to which the present invention pertains should be able to understand that various modifications and alterations can be made without departing from the technical spirit or essential features of the present invention. Therefore, it should be understood that the disclosed embodiments are not limiting but illustrative in all aspects. The scope of the present invention is defined not by the above description but by the following claims, and it should be understood that all changes or modifications derived from the scope and equivalents of the claims fall within the scope of the present invention.

What is claimed is:

1. An electronic nose apparatus based on spectrum analysis, the electronic nose apparatus comprising:
   a radio frequency (RF) resonator configured to receive a test sample and output a resonating RF having a spectrum generated by resonating an applied RF with the test sample;
   an impinger configured to emit the test sample, which is liquefied by concentrating a gaseous sample whose smell is to be measured into a solvent, to the RF resonator; and
   a signal generator/analyzer configured to apply the RF into the RF resonator and receive and analyze the resonating RF output from the RF resonator through the resonance.

2. The electronic nose apparatus of claim 1, further comprising an air pump configured to supply air to the impinger in order to emit the test sample liquefied in the impinger.

3. The electronic nose apparatus of claim 1, wherein the solvent used in the impinger is water when the gaseous sample is soluble in water and is acetone when the gaseous sample is soluble in fat.

4. The electronic nose apparatus of claim 1, wherein the RF resonator is manufactured so that the RF applied into the RF resonator does not escape from the RF resonator and forms a preset resonance mode in the RF resonator.

5. The electronic nose apparatus of claim 1, wherein the RF applied into the RF resonator has a frequency band of 8 GHz to 35 GHz.

6. The electronic nose apparatus of claim 1, wherein the RF resonator comprises:
   a sample inlet through which the test sample is introduced from the impinger into the RF resonator;
   an RF reception (RX) terminal through which the RF is applied from the signal generator/analyzer into the RF resonator; and
   an RF transmission (TX) terminal through which the resonating RF is output to the signal generator/analyzer.

7. The electronic nose apparatus of claim 1, wherein the RF applied into the RF resonator is applied from the signal generator/analyzer to the RF resonator through a reception (RX) antenna, and
   the resonating RF output from the RF resonator is transferred to the signal generator/analyzer through a transmission (TX) antenna.

8. The electronic nose apparatus of claim 7, wherein the RX and TX antennas are wire cables.

9. The electronic nose apparatus of claim 7, wherein the RX and TX antennas are connected to the signal generator/analyzer in a wireless manner.

10. The electronic nose apparatus of claim 7, wherein the RX and TX antennas are circular antennas connected to the signal generator/analyzer in a wireless manner, and
    diameters of the RX and TX antennas are a maximum width of the RF resonator or less.

11. The electronic nose apparatus of claim 1, wherein the signal generator/analyzer analyzes an absorptivity of the spectrum of the resonating RF output from the RF resonator using an S21 Mode.

12. The electronic nose apparatus of claim 1, wherein the signal generator/analyzer is one of a vector network analyzer (VNA) and a scalar network analyzer (SNA).

13. A method of implementing an electronic nose on the basis of spectrum analysis, the method comprising:
    a radio frequency (RF) resonance operation of receiving a test sample whose smell is to be measured, receiving an RF, and outputting a resonating RF having a spectrum generated by resonating the received RF with the test sample; and
    a spectrum analysis operation of receiving the resonating RF output after the RF resonance operation is performed and analyzing the spectrum of the resonating RF,
    wherein the test sample is a gaseous sample and is concentrated in a liquid solvent and liquefied.

14. The method of claim 13, wherein the RF resonance operation is performed in an RF resonator manufactured so that the RF applied into the RF resonator does not escape from the RF resonator and forms a preset mode in the RF resonator.

15. The method of claim 13, wherein the RF applied in the RF resonance operation has a frequency band of 8 GHz to 35 GHz.

16. The method of claim 13, wherein the spectrum analysis operation comprises analyzing an absorptivity of the spectrum of the resonating RF output in the RF resonance operation using an S21 Mode.

* * * * *